US006017949A

United States Patent [19]

D'Amato et al.

[11] Patent Number: 6,017,949
[45] Date of Patent: Jan. 25, 2000

[54] METHOD OF REGULATING THE FEMALE REPRODUCTIVE SYSTEM THROUGH ANGIOGENESIS INHIBITORS

[76] Inventors: Robert J. D'Amato, 65 Huron Ave., Cambridge, Mass. 02138; Nancy Klauber Demore, 32C Scott Cir., Hanscom, AFB, 01731

[21] Appl. No.: 08/904,708

[22] Filed: Aug. 1, 1997

Related U.S. Application Data

[60] Provisional application No. 60/023,385, Aug. 2, 1996, abandoned.

[51] Int. Cl.⁷ .................................................. A61K 31/335
[52] U.S. Cl. ............................................................. 514/450
[58] Field of Search ............................................. 514/450

[56] References Cited

U.S. PATENT DOCUMENTS 4,599,331  7/1986  Schreiber .

FOREIGN PATENT DOCUMENTS

| 0 144 589 | 8/1984 | European Pat. Off. . |
| 0 378 364 | 7/1990 | European Pat. Off. . |
| WO 91/19731 | 12/1991 | WIPO . |
| WO 94/20128 | 9/1994 | WIPO . |
| WO 95/33050 | 12/1995 | WIPO . |
| WO 97/15666 | 5/1997 | WIPO . |

OTHER PUBLICATIONS

Klauber, N. et al., "Critical Components of the Female Reproductive Pathway are Suppressed by the Angiogenesis Inhibitor AGM–1470", *Nature Medicine*, vol. 3, No. 4, pp. 443–446 (1997).
Abe, J. et al., A Fumagillin Derivative Angiogenesis Inhibitor, AGM–1470, Inhibits Activation of Cyclin–Dependent Kinases and Phosphorylation of Retinoblastoma Gene Product but not Protein Tyrosyl Phosphorylation of Protooncogene Expression in Vascular Endothelial Cells, *Cancer Research*, vol. 54, No. 13, pp. 3407–3412 (1994).
Brem, H. et al., "Interstitial Chemotherapy with Drug Polymer Implants for the Treatment of Recurrent Gliomas", *Journal of Neurosurgery*, vol. 74, pp. 441–46 (1991).
Champlin, A.K. et al., "Determining the Stage of the Estrous Cycle in the Mouse by the Appearance of the Vagina", *Biology of Reproduction*, vol. 8, pp. 491–494 (1973).
Christenson, L.K. et al., "Proliferation of Microvascular Endothelial Cells in the Primate Corpus Luteum during the Menstrual Cycle and Simulated Early Pregancy", *Endocrinology*, vol. 137, No. 1, pp. 367–374 (1996).
Christofferson, R. H. et al., "Morphology of the Endometrial Microvasculature During Early Placentation in the Rat", *Cell and Tissue Research*, vol. 253, No. 1, pp. 209–220 (1988).
Connolly, D. T. et al., "Human Vascular Permeability Factor", *The Journal of Bilogical Chemistry*, vol. 264, No. 23, pp. 20017–20024 (1989).
D'Amato, R.J. et al., "Thalidomide is an Inhibitor of Angiogenesis", *Proceedings of National Academy of Sciences*, vol. 91, pp. 4082–4085 (1994).

Ferrara, N. et al., "Pituitary Follicular Cells Secrete a Novel Heparin–Binding Growth Factor Specific for Vascular Endothelial Cells", *Biochemical and Biophysical Research Commuications*, vol. 161, pp. 851–858 (1989).
Folkman, J. et al., "Angiogenic Factors", *Science*, vol. 235, pp. 442–447 (1987).
Goodger, A.M. et al., "Uterine Endothelial Proliferation Before and After Embryo Implantation", *Journal Reproduction Fertility*, vol. 99, pp. 451–457 (1993).
Gospodarowicz, D. et al., "Isolation and Characterization of a Vascular Endothelial Mitogen Produced by Pituitary–Derived Folliculo Stellate Cells", *Proceedings of the National Academy of Sciences*, vol. 86, pp. 7311–7315 (1989).
Gospodarowicz, D. et al., "Production of a Corpus Luteum Angiogenic Factor Responsible for the Proliferation of Capillaries and Neovascularization of the Corpus Lutem", *Proceedings of the National Academy of Sciences*, vol. 75, pp. 847–851 (1978).
Greenwald, G.S., "Temporal and Topographic Changes in DNA Synthesis after Follicular Atresia", *Biology o Reproduction*, vol. 41 (1), pp. 175–181 (1989).
Jakob, W. et al., "Demonstration of Angiogenesis Activiity in the Corpus Luteum of Cattle", *Experimental Pathology*, vol. 13, pp. 231–236 (1977).
Kamat, B.R. et al., "Expression of Vascular Permeability Factor/Vascular Endothelial Growth Factor by Human Granulosa and Theca Lutein Cells", *American Journal o Pathology*, vol. 146, pp. 157–165 (1995).
Keck, P.J. et al., "Cascular Permeability Factor, an Endothelial Cell Mitogen Related o PDGF", *Science*, vol. 246, pp. 1309–1312 (1989).
Koos, R.D. et al., "Expression of Basic Fibroblast Growth Factor in the Rat Ovary: Detection of mRNA using Reverse Transcription–Polymerase Chain Amplification", *Molecular Endocrinology*, vol. 3, No. 12, pp. 2041–2048 (1989).
Koos, R.D. et al., "Factors that May Regulate the Growth and Regression of Blood Vessels in the Ovary", *Seminars in Reproductive Endocrinology*, vol. 1, pp. 295–307 (1983).
Neufeld, G. et al., "Bovine Granulosa Cells Produce Basic Fibroblast Growth Factor", *Endocrinology*, vol. 121, pp. 597–603 (1987).
Poole, T.J. et al., "Vasculogenesis and Angiogenesis: Two Distinct Morphogenetic Mechanisms Establish Embryonic Pattern", *Journal of Experimental Zoology*, vol. 251, pp. 224–231 (1989).

(List continued on next page.)

*Primary Examiner*—Russell Travers
*Attorney, Agent, or Firm*—Jones & Askew, LLP

[57] ABSTRACT

A method of inhibiting angiogenesis in a female mammal to regulate fertility comprising administering to the female mammal an effective amount of an angiogenesis inhibiting compound. In addition, a method of inhibiting angiogenesis in a female mammal to treat a disease or condition of the reproductive tissue that is mediated by angiogenesis comprising administering to the female mammal an effective amount of an angiogenesis inhibiting compound. AGM-1470 is provided as such an angiogenesis inhibiting compound.

8 Claims, 12 Drawing Sheets

OTHER PUBLICATIONS

Tsukada et al. "Neovascularization of the Corpus Luteum of Rats During the Estrus Cycle", *Pathology International*, vol. 46 (6), pp. 408–416 (1996).

Ravindranath, N. et al., "Vascular Endothelial Growth Factor Messenger Ribonucleic Acid Expression in the Primate Ovary", *Endocrinology*, vol. 131, pp. 254–260 (1992).

Redmer, D.A. et al., "Evidence for a Non–Steroidal Angiotropic Factor from the Primate Corpus Luteum: Stimulation of Endothelial Cell Migration in Vitro", *Proceedings of the Society for Expermental Biology and Medicine*, vol. 179, pp. 136–140 (1985).

Schlaeger, T.M. et al., "Vascular Endothelial Cell Lineage–Specific Promoter in Transgenic Mice", *Development*, vol. 121, pp. 1089–1098 (1995).

Shweiki, D. et al., "Patterns of Expression of Vascular Endothelial Growth Factor and VEFG Receptors in Mice Suggest a Role in Hormonally Regulated Angiogenesis", *Journal of Clinical Investigation*, vol. 91, pp. 2235–2243 (1995).

Tamura, H. et al., "Angiogenesis and Its Hormonal Control in the Corpus Luteum of the Pregnant Rat", *Biology of Reproduction*, vol. 36, pp. 1149–1154 (1987).

Torry, R. et al., "Angiogenesis in the Uterus: Potential Regulation and Relation to Tumor Angiogenesis", *American Journal of Reproductive Immunology*, vol. 27, pp. 171–179 (1992).

Yanagashita, M. et al., "Biosynthesis of Proteoglycans by Rat Granulosa Cells Cultured In Vitro: Modulation by Gonadotropins, Steroid Hormones, Protaglandins and Cyclic Nucleotide", *Endocrinology*, vol. 109, pp. 1641–1649 (1981).

Zeleznik, A.J. et al., "Gonadotropin–Binding Sites in the Rhesus Monkey Ovary: Role of the Vasculature in the Selective Distribution of Human Chorionic Gonadotropin to the Preovulatory Follicle", *Endrocinology*, vol. 109, pp. 356–362 (1981).

Merck Manual 16th ed, pp. 1808–1809 Beichow et al Ed, Merck & Co Rahway NJ, 1992.

Ingker et al, Nature, vol. 348, pp. 555–557 Dec, 6, 1990.

Toguebage et al 99 CA:83611t, 1983.

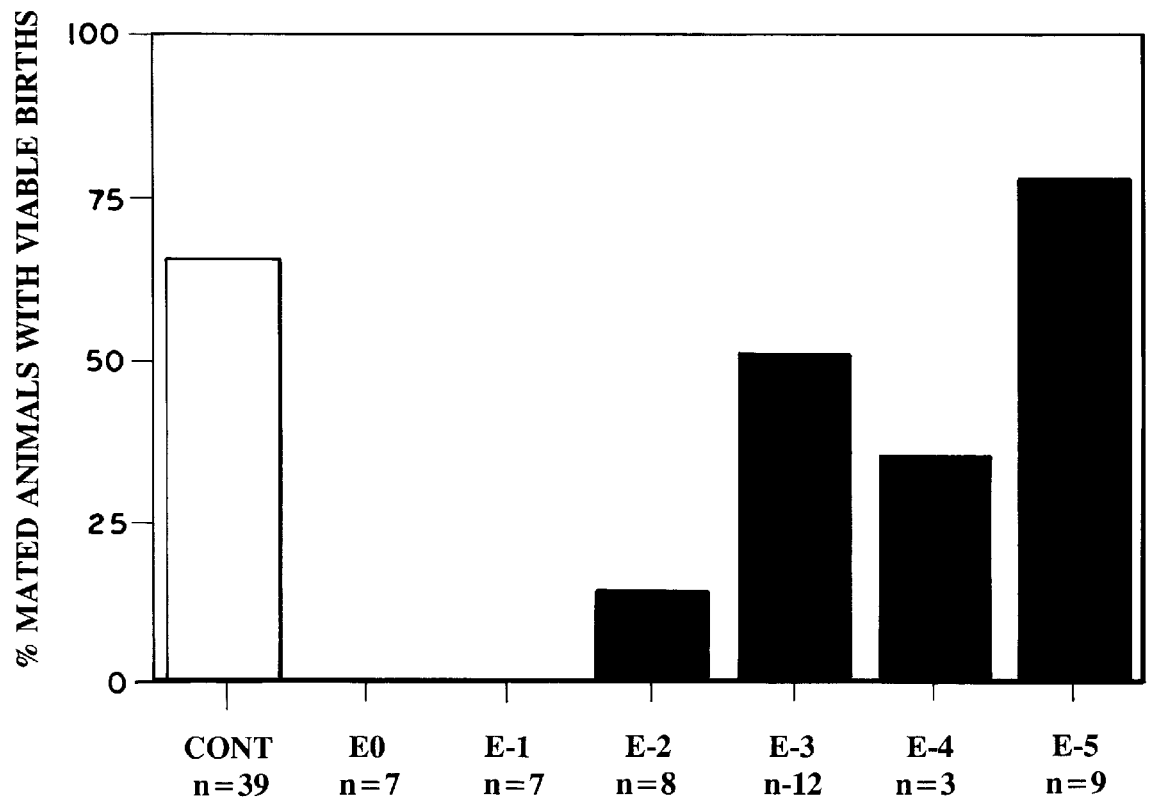
Fig_8

METHOD OF REGULATING THE FEMALE REPRODUCTIVE SYSTEM THROUGH ANGIOGENESIS INHIBITORS

CROSS-REFERENCE TO RELATED APPLICATION

This application claims priority to U.S. Provisional Application Ser. No. 60/023,385, filed Aug. 2, 1996 now abandoned.

FIELD OF THE INVENTION

The present invention relates to the use of angiogenesis inhibiting compounds to reversibly inhibit the female mammalian reproductive system. These angiogenesis inhibiting compounds are capable of controlling fertility, terminating a pregnancy, as well as controlling pathological conditions and disorders of the female reproductive system.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, the female reproductive cycle and embryonic development.[1] Angiogenesis is also critical in the progression of many disease states, such as hemangioma, endometriosis, solid tumors and macular degeneration.

Through angiogenesis, endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Angiogenesis occurs during the cyclical changes of the female reproductive system. In preparation for fertilization, the theca interna of the ovaries becomes richly vascularized to support the growth of a follicle. During ovulation, the follicle ruptures and an egg is released to the uterus. If fertilization occurs, the ruptured follicle then is invaded by thecal vessels and forms the corpus luteum. The corpus luteum releases hormones that regulate reproductive processes, including the thickening of the endometrium for the implantation of the fertilized ovum. After the blastocyst implants in the endometrium, the placenta develops and provides nutrients for the growing embryo. Throughout all of these stages of mammalian reproduction, angiogenesis is critical to further development.

Specifically, angiogenesis occurs during follicular growth, formation of the corpus luteum, growth of the endometrium, and development of the placenta and embryo after conception.[1,2,3,4] These angiogenic episodes are self-limiting and presumably tightly regulated. During the menstrual cycle, the spiral arteries undergo substantial anatomical changes. As the endometrium thickens three to five fold during the next menstrual cycle, the remnants of the spiral arteries must undergo substantial growth and give rise to a new capillary bed in order to maintain the integrity of the rapidly growing stroma. This uterine angiogenesis provides an existing vascular supply for the trophoblast to invade if fertilization of the ovum occurs. Following fertilization, the first stage of implantation is the adhesion of the blastocyst to the endometrial epithelium. This is followed by the penetration of the trophoblast through the epithelial lining.[7]

Physiological changes in the ovary are especially critical for the proper functioning of the female reproductive cycle. In the ovary, during the course of follicular growth, the theca interna becomes richly vascularized. Follicular maturation is associated with increasing angiogenesis, whereas follicles undergoing atresia are associated with decreasing vascularity.[8] Following ovulation, growth factors are expressed which induce the thecal vessels to grow and invade the ruptured follicle and form a complex capillary network which nourishes the developing corpus luteum.[9,10,11,2,12] Approximately 50% of the cells of the mature bovine corpus luteum are endothelial cells, and in the primate corpus luteal endothelial cells comprise 85% of proliferating cells.[4]

The mitotic activity of these endothelial cells is highest during the early luteal phase, persists but declines during the midluteal phase and is minimal during luteal regression. Corpus luteal maintenance during pregnancy is associated with continued angiogenesis.[4] This has been demonstrated in the pregnant rat where the labeling index of endothelial cells in the corpus luteum increases and peaks on embryonic day 14 (E14) which correlates with further growth of the corpus luteum.[5] Angiogenesis and its hormonal control in the corpus luteum of the pregnant rat.[13] Thus, the exponential growth of the corpus luteum is associated with aggressive neovascularization. This vasculature plays a vital role in providing nutrients and trophic factors to and transporting secreted hormones from the developing follicle and corpus luteum.[14]

The factors controlling ovarian angiogenesis are just beginning to be fully understood. Two growth factors demonstrated in the ovary are basic fibroblast growth factor (bFGF) and vascular endothelial growth factor (VEGF). Cultured granulosa cells produce bFGF, the release of which may be modulated by heparin sulfate proteoglycans which are produced under gonadotropin modulation. Recent evidence suggests that vascular endothelial growth factor (VEGF), an endothelial cell specific mitogen and permeability factor, may play an integral role in ovarian angiogenesis.[15,16,17]

VEGF, a secreted homodimeric glycoprotein, is under gonadotropin control. It is both temporally and spatially correlated with active angiogenesis in the theca and the corpus luteum. Thus, as is the case with other tissues throughout the body, the ovary has multiple stimulators of angiogenesis including.

VEGF and bFGF which are likely to be in balance with endogenous inhibitors to achieve the appropriate level of blood vessel growth.[18,19,20,21,22,23] In addition, the uterus undergoes dramatic physiological changes in the course of the female reproductive cycle. Under hormonal regulation by estrogen and progesterone, the uterus undergoes differentiation into a structure which is capable of supporting the implantation of a blastocyst. The cyclical maturation of the endometrium in the uterus is driven by the mitogenic activity of the spiral arteries. Following implantation, the maternal spiral arteries within the endometrium are invaded by trophoblasts that adhere to and migrate along the surface of the vascular endothelial cells.

Currently, biochemical female reproductive control is primarily accomplished through regimens of hormones such as estrogen and progesterone. Although this method of birth control is quite effective in preventing pregnancy, there are many side effects to the administration of additional hormones. Often such forms of birth control cause emotional and physiological disturbances, resulting in mood shifts or loss of libido. Health risks such as stroke and heart problems increase for women who smoke while using hormonal birth control. In addition, these forms of fertility control are only potent when taken on a regularly basis. The administration of hormones is advised to be discontinued should fertilization occur to diminish chances of health complications.[24]

Many factors, chemical as well as mechanical, have been shown to be capable of promoting or inhibiting angiogenesis in vivo and in vitro.[25] Although the presence of angiogenesis promoting factors during growth and development of the ovaries, uterus, and placenta have been evaluated, the effects of angiogenesis inhibiting factors on these organs have not be elucidated. Since angiogenesis is an important component in the female reproductive system, it might be possible to regulate reproductive processes with angiogenesis inhibiting factors.

There are a large number of known angiogenesis inhibiting compounds which will undoubtedly continue to grow as scientific research continues. Some of the currently known angiogenesis inhibiting compounds are: AGM-1470 (TNP-470) or antagonists to one of its receptors MetAP-2; growth factor antagonists or antibodies to growth factors (including VEGF or bFGF); growth factor receptor antagonists or antibodies to growth factor receptors; inhibitors of metalloproteinases including TIMP, batimastat (BB-94), and marimastat; tyrosine kinase inhibitors including genistein and SU5416; integrin antagonists including antagonists alphaVbeta3/5 or antibodies to integrins; retinoids including retinoic acid or the synthetic retinoid fenretinide; steroids 11α-epihydrocortisol, corteloxone, tetrahydrocortisone and 17α-hydoxyprogesterone; protein kinase inhibitors including staurosporine and MDL 27032; vitamin D derivatives including 22-oxa-1 alpha, and 25-dihydroxyvitamin D3; arachidonic acid inhibitors including indomethacin and sulindac; tetracycline derivatives including minocycline; thalidomide derivatives; 2-methoxyestradiol; tumor necrosis factor-alpha; interferon-gamma-inducible protein 10 (IP-10); interleukin 1 and interleukin 12; interferon alpha, beta or gamma; angiostatin™ protein or plasminogen fragments; endostatin™ protein or collagen 18 fragments; proliferin-related protein; group B streptococcus toxin; CM101; CAI; troponin I; squalamine; nitric oxide synthase inhibitors including L-NAME; thrombospondin; wortmannin; amiloride; spironolactone; ursodeoxycholic acid; bufalin; suramin; tecogalan sodium; linoleic acid; captopril; irsogladine; FR-118487; triterpene acids; castanospermine; leukemia inhibitory factor; lavendustin A; platelet factor-4; herbimycin A; diaminoantraquinone; taxol; aurintricarboxylic acid; DS-4152; pentosan polysulphite; radicicol; fragments of human prolactin; erbstatin; eponemycin; shark cartilage; protamine; Louisianin A, C and D; PAF antagonist WEB 2086; auranofin; ascorbic ethers; and sulfated polysaccharide D 4152.

AGM-1470 (O-chloroacetylcarbamoyl fumagillol) is an analog of fumagillin with well-described angiogenesis inhibiting activities that is highly selective, potent, and non-toxic.[26] AGM-1470 inhibits endothelial cell proliferation at concentrations that are inactive for other cell types.[27] Fumagillin is a chemical produced by *Aspergillus fumigatus* which acts as a potent angiogenesis inhibitor in vitro and in vivo. AGM-1470 is 50 times more active and much less toxic than the parent compound. It potently inhibits endothelial proliferation and migration as well as angiogenesis in the chick chorioallantoic membrane. AGM-1470 has shown marked antineoplastic activity in animal models and is in clinical trials for the treatment of human neoplastic tumors and other angiogenic disorders.

Although shown to be an effective inhibitor of tumor angiogenesis, angiogenesis inhibiting compounds have not heretofore been shown to be effective in inhibiting angiogenesis in female reproductive and embryonic tissues. The angiogenesis of female reproductive tissues differs from angiogenesis in other tissues, such as in a tumor, as they are affected by different growth factors and under different regulatory mechanisms. Additionally, inhibition of angiogenesis in the female reproductive system has not heretofore been shown to disrupt or regulate critical events in the reproductive cycle. Thus, the successful use of angiogenesis inhibitors for contraception or treatment of disease in the tissues of the female reproductive system has not been previously demonstrated as possible, effective, safe, and without irreversible effects on the female reproductive system.

Another impediment to the use of angiogenesis inhibitors as contraceptives relates to the possible risk of inducing birth defects if contraception fails. This concern derives from the recent observation that thalidomide is an angiogenesis inhibitor.[28] Thalidomide produces unique birth defects when mothers ingest the drug during the first trimester. However, we believed that thalidomide had a unique capacity to induce limb defects by specific interaction with receptors in the limbs and through local concentration of the drug in the limbs. Therefore, we attempted herein to establish that other angiogenesis inhibitors can be used as contraceptives without inducing birth defects.

It is clear that angiogenesis plays a major role in the events encompassing reproduction. Proliferation of blood vessels is seen coincident with ovulation, corpus luteal growth, decidualization and placental formation. If this angiogenic activity could be reversibly repressed or eliminated, fertility and pathological reproductive disorders could be controlled. What is needed, therefore, is to demonstrate that angiogenesis inhibitors can inhibit the female reproductive system, without side-effects or irreversibility of the physiological changes.

SUMMARY OF THE INVENTION

In accordance with the present invention, compositions and methods are provided that are effective for modulating angiogenesis, and inhibiting unwanted angiogenesis, especially angiogenesis related to female reproduction and pathological reproductive disorders. The present invention includes application of angiogenesis inhibitors, such as AGM-1470, and other antagonists of AGM-470 receptor MetAP-2. AGM-1470 comprises an antibiotic-derivative (O-chloroacetylcarbamoyl fumagillol) for use as an angiogenesis inhibiting compound. AGM-1470, also known as TNP-470, is a highly selective, potent, and non-toxic angiogenesis inhibitor.

The present invention is contemplated to be applicable for administration to fertile female mammals for control of reproduction, as well as administration to either fertile or infertile female mammals for treatment of conditions and disorders of the reproductive system. The compositions are administerable to both humans and animals, as may be applicable.

The present invention provides methods and compositions for controlling angiogenesis prior to and during decidualization, placental formation, yolk sack development and cyclical endometrial maturation, which are angiogenesis dependent, for the regulation of the female reproductive processes.

Applicable systems are delineated which inhibit angiogenesis in the uterus, ovary, placenta, or fetus.

Depending on when the angiogenesis inhibiting compound is administered and under what regimen, the invention may function through a number of different mechanisms for deterrence of a pregnancy. The invention inhibits angiogenesis in the ovary, obstructing the development of requisite vascularization, thereby preventing ovulation or the normal release of hormones necessary for conception, and functioning as a prophylactic to conception. In addition, the compound inhibits angiogenesis in the uterus, preventing the formation and engorgement of the tissue necessary for implantation, thereby obliterating the necessary conditions for the maturation of the blastocyst. Therefore, the administration of the angiogenesis inhibiting compound may be before or after intercourse and fertilization have occurred, thus providing an effective method of birth control. Furthermore, the invention interferes with the placental and yolk sack development, as well as disrupting vascular development in the embryo, thereby preventing further development of the embryo and continuation of the pregnancy. Therefore, the invention may also function to initiate spontaneous termination of a pregnancy.

In one embodiment, the present invention provides a methodology for use of AGM-1470, and functional analogs thereof, which produce no signs of toxicity to the mother and allows for recovery of reproductive function. Thus, AGM-1470 provides for the effective disruption of decidualization, preventing the accompanying vascularization of the endometrium, placental formation, and fetal development, by angiogenesis inhibition without adverse effects to the mother.

The present invention also relates to a system for the application of angiogenesis inhibitors, such as AGM-1470, and functional analogs thereof, on non-pregnant female tissues for interference of endometrial angiogenesis with reduced endometrial glandular and stromal proliferation. The inhibitory effect of AGM-1470, for example, on endometrial angiogenesis, stromal and glandular proliferation, as well as placental formation, can treat several pathological reproductive processes such as endometriosis, adenomyosis, dysfunctional uterine bleeding, uterine leiomyoma (fibroids), and choriocarcinoma. In addition, the inhibition of the vascularization of the mucosa of the uterine tube interferes with the implantation of the blastocyst in this portion of the female reproductive tract. Thus, the application of an angiogenesis inhibiting compound may also prevent ectopic pregnancy.

Accordingly, it is an object of the present invention to provide methods of regulating the female reproductive system with compositions comprising angiogenesis inhibitors, which include for example AGM-1470, or other antagonists to the AGM-1470 receptor MetAP-2.

It is another object of this invention is to provide a method for controlling fertility by administering an effective amount of an angiogenesis inhibiting compound, either in single or multiple doses, capable of preventing conception or terminating a pregnancy. The angiogenesis inhibiting compound may be administered prior to intercourse, after intercourse or after ovum fertilization.

It is yet another object of the present invention to provide a therapy for reproductive disorders and control of reproduction that has minimal side effects.

BRIEF DESCRIPTION OF THE FIGURES

FIGS. 1A, 1B, and 1C show the normal pattern of growth of fetuses on E9, E13 and E18. When AGM-1470 mg/kg s.c. was given on E1 there was initial growth to E9 (FIG. 1D), followed by failure of further growth with resorption (FIGS. 1E & 1F). When AGM-1470 30 mg/kg s.c. was given on E7 there was initial growth to E9 (FIG. 1G) followed by hemorrhage around the implantation sites by E13 (FIG. 1H) and resorption by E18 (FIG. 1I). Ruler at the bottom of each panel shows mm intervals.

FIG. 2A shows control embryo and placenta at 25×. FIG. 2B shows control placenta at 100× demonstrating an extension of nucleated red blood cells into the fetal placenta (see arrows). FIG. 2C shows AGM-1470 rejected on E1 resulted in a small, disorganized embryo. FIG. 2D shows the loss of invasion of blood islands and nucleated red blood cells in the placenta. FIG. 2E shows that AGM-1470 injected on E7 resulted in reduced nucleated red blood cells in the embryo. FIG. 2F shows reduced nucleated red blood cells in the fetal placenta with reduced labyrinth structure of the placenta. (P—placenta, D=decidua).

FIG. 3A shows tissue from control animal at 2.5× magnification. FIG. 3B shows tissue from AGM-1470 treated animal at 2.5× magnification. Note the decreased size and number of corpora lutea (small arrows) and number of endometrial glands (large arrows) in treated mice.

FIG. 3C shows a close up of ovary section from FIG. 1A at 10× magnification showing corpora lutea (large arrows) and small antral follicles. FIG. 3D shows a close up of ovary from FIG. 1B at 10× magnification showing regressed corpora lutea and thin layer of granulosa cells in large antral follicles (small arrows).

FIG. 4A shows the immunohistochemical staining with antibodies to PCNA demonstrating a high decree of positively staining stromal cells in the control decidua (630×, arrows point to examples of positively stained cells). FIG. 4B shows that the decidua from mice treated with AGM-1470 on E1 has a decreased number of positively staining cells (630×). FIG. 4C shows the immunohistochemical staining with antibodies to Factor VIII demonstrating a high microvessel density in the control intersite endometrium (250×) versus FIG. 4D where the specimen injected on E1 with AGM-1470 (250×).

(FIGS. 6A and 6B at 100× magnification, scale bar=160µ, arrows point to glands). Immunohistochemical staining with antibodies to PCNA revealed a 68% decrease in the proliferation rate of endometrial stromal cells and a 67% decrease of proliferating glandular epithelial cells in the AGM-1470 treated uteri (FIG. 6D) as compared to control (FIG. 6C). (FIGS. 6C and 6D at 630× magnification, arrows point to examples of positively staining glandular cells). Immunohistochemical analysis with antibodies to factor VIII demonstrated a 41% decrease in the microvessel density in AGM-1470 treated uteri (FIG. 6F) as compared to control (FIG. 6E) (FIGS. 6E and 6F at 250× magnification, arrows point to microvessels).

FIG. 7A shows tissue from control animal at 2.5× magnification. FIG. 7B. shows tissue from treated animal at 2.5× magnification. Thin arrows indicate the corpora lutea. The fat arrows indicate implantation sites in control animals not seen in AGM-1470 treated animal.

FIG. 8 shows the effect of a single-dose of AGM-1470 on the percentage of mated animals with viable births. Group housed female C57BL/6 mice were treated with a single injection of AGM-1470 (30 mg/kg, s.c.) and paired with male breeders at various times after treatment. Treatment groups are designated as the number of days between plugging and treatment. The 6 control groups are combined and expressed as the mean±SD. The number of matings in per group is listed below each labeled group. Note the inhibition of viable births with treatments on E0, E−1, and E−2.

DETAILED DESCRIPTION OF THE INVENTION

Figure 1:
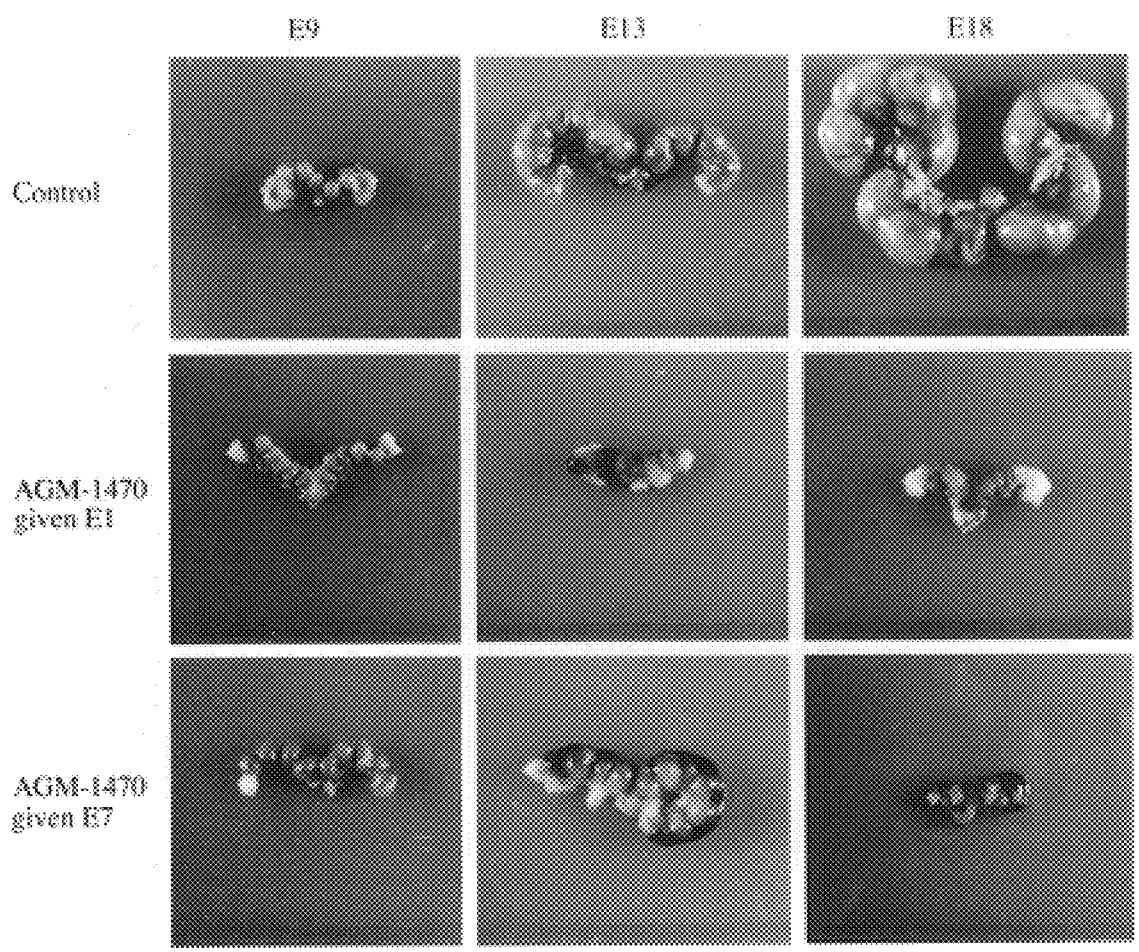
FIGS. 1A–1I show the gross morphology of gravid mouse uteri. Inseminated mice were treated with AGM-1470 30 mg/kg s.c. or saline on Embryonic day 1 (E1) or E7, and mice were sacrificed at E9, 13 or 18.

The present invention includes compositions and methods for the regulation of the female reproductive system and the treatment of reproductive diseases and conditions that are mediated by or associated with angiogenesis. By "female reproductive system" is meant to include physiologic mechanisms and living tissues by which female mammals prepare for and produce offspring. By "female reproductive tissue" is meant to include the cells, blood vessels and organs involved in the female reproductive system, including the ovary, uterus, fetus or placenta, or tissues originating therefrom (for example, ectopic endometrial tissue).

The present invention includes any of the known angiogenesis inhibitors, and those discovered in the future, to be used as reproductive regulators or to treat abnormal reproductive conditions. Examples of known angiogenesis inhibitors include: AGM-1470 (TNP-470) or antagonists to one of its receptors MetAP-2; growth factor antagonists or antibodies to growth factors (including VEGF or bFGF); growth factor receptor antagonists or antibodies to growth factor receptors; inhibitors of metalloproteinases including TIMP, batimastat (BB-94), and marimastat; tyrosine kinase inhibitors including genistein and SU5416; integrin antagonists including antagonists alphaVbeta3/5 or antibodies to integrins; retinoids including retinoic acid or the synthetic retinoid fenretinide; steroids 11α-epihydrocortisol, corteloxone, tetrahydrocortisone and 17α-hydoxyprogesterone; protein kinase inhibitors including staurosporine and MDL 27032; vitamin D derivatives including 22-oxa-1 alpha, and 25-dihydroxyvitamin D3; arachidonic acid inhibitors including indomethacin and sulindac; tetracycline derivatives including minocycline; thalidomide derivatives; 2-methoxyestradiol; tumor necrosis factor-alpha; interferon-gamma-inducible protein 10 (IP-10); interleukin 1 and interleukin 12; interferon alpha, beta or gamma; angiostatinTM protein or plasminogen fragments; endostatinTM protein or collagen 18 fragments; proliferin-related protein; group B streptococcus toxin; CM101; CAI; troponin I; squalamine; nitric oxide synthase inhibitors including L-NAME; thrombospondin; wortmannin; amiloride; spironolactone; ursodeoxycholic acid; bufalin; suramin; tecogalan sodium; linoleic acid; captopril; irsogladine; FR-118487; triterpene acids; castanospermine; leukemia inhibitory factor; lavendustin A; platelet factor-4; herbimycin A; diaminoantraquinone; taxol; aurintricarboxylic acid; DS-4152; pentosan polysulphite; radicicol; fragments of human prolactin; erbstatin; eponemycin; shark cartilage; protamine; Louisianin A, C and D; PAF antagonist WEB 2086; auranofin; ascorbic ethers; and sulfated polysaccharide D 4152.

More particularly, the present invention relates to a method of inhibiting angiogenesis in a female mammal to regulate fertility comprising administering to the female mammal an effective amount of a fertility regulating angiogenesis inhibiting compound, wherein the compound is administered either to prevent conception or to terminate a pregnancy. In order to accomplish either of these two objectives, the angiogenesis inhibiting compound may be administered in a single dose or in multiple doses. The compound may be administered prior to intercourse, after intercourse or after ovum fertilization, in order to inhibit angiogenesis in the uterus, ovary, placenta or embryo.

Depending on when the compound is administered and under what regimen, the invention functions through a number of different modalities. The invention inhibits angiogenesis in the ovary, obstructing the development of requisite vascularization, thereby preventing the normal release of hormones necessary for conception, and functioning as a prophylactic to conception. In addition, the compound inhibits angiogenesis in the uterus, preventing the formation and engorgement of the tissue necessary for implantation, thereby obliterating the necessary conditions for the maturation of the blastocyst.

The invention provides for the first time that it is possible to use an angiogenesis inhibiting compound to regulate fertility and treat conditions of the female reproductive tissues. The invention provides a methodology for use of, for example AGM-1470, which produces no signs of toxicity to the mother and allows for recovery of reproductive function. Thus, AGM-1470 for example prevents vascularization of the endometrium (disrupting decidualization), placental formation, and fetal development, by angiogenesis inhibition without adverse effects to the mother.

In addition, the present invention relates to a system for treating a female mammal with a disease or condition of the reproductive tissue that is mediated by angiogenesis. This method provides for the application of an angiogenesis inhibiting compound, such as AGM-1470, in non-pregnant female mammals for interference of endometrial angiogenesis with reduced endometrial glandular and stromal proliferation. The inhibitory effect of an angiogenesis inhibiting compound, such as AGM-1470, on endometrial angiogenesis, stromal and glandular proliferation, as well as placental formation, can treat several pathological reproductive processes such as endometriosis, adenomyosis, dysfunctional uterine bleeding, uterine leiomyoma (fibroids), and choriocarcinoma. In addition, the inhibition of the vascularization of the mucosa of the uterine tube interferes with the implantation of the blastocyst in this portion the female reproductive tract. Thus, the application of an anglogenesis inhibiting compound may also prevent ectopic pregnancy.

The present invention includes any angiogenesis inhibiting compound which can be effectively used to regulate fertility or treat a condition of the female reproductive tissues. One such compound is an antibiotic-derivative designated as AGM-1470 (O-chloroacetylcarbamoyl fumagillol).[1] AGM-1470, also known as TNP-470, is highly selective, potent, and non-toxic. AGM-1470 is an analog of fumagillin, is a potent inhibitor of endothelial cell migration, endothelial cell proliferation and capillary tube formation, but has not heretofore been shown to be an effective inhibitor of angiogenesis in the tissues of female reproductive system. Fumagillin is a naturally secreted antibiotic of *Aspergillus Fumigatus fresenius*. Fumagillin itself suppresses angiogenesis and neovascularization but its effectiveness as a pharmaceutical is limited because it produces side effects including severe weight loss. Analogs of fumagillin have been developed which retain the potent angiogenesis inhibiting activity of fumagillin without producing side effects. AGM-1470 is 50 times more active and much less toxic than the parent compound, suppressing angiogenesis without the usual toxic side effects associated with conventional chemotherapy drugs.

Fumagillin may be isolated from in vitro cultures of *Aspergillus Fumigatus fresenius*, often cultured on capillary endothelial cells. Fumagillol is then produced by alkaline hydrolysis of fumigillan. AGM-1470 then can be isolated from fumagillol, from which over one hundred other derivatives are synthesized. Therefore, the invention contemplates that other analogs of fumagillin similar to AGM-1470 would be expected to be useful in the present invention. Furthermore, AGM-1470 is believed to inhibit angiogenesis through its interaction with a receptor designated MetAP-2. Therefore, the invention contemplates that other MetAP-2 receptor antagonists or agonists would be expected to be useful in the present invention.

Although shown to be effective in the inhibition of tumor angiogenesis, angiogenesis inhibiting compounds, such as AGM-1470, were not previously known to be effective to regulate female reproductive tissues. Angiogenesis in the female reproductive tissues differs from angiogenesis in cancerous tissues, as it is affected by different growth factors and is under different regulatory mechanisms. Therefore, there was formerly no expectation for the successful use of angiogenesis inhibitors in female reproductive tissues to inhibit angiogenesis and to effectively regulate the reproductive system or treat diseases or conditions of the reproductive tissues. It had not been demonstrated that these compounds could be used safely, without irreversible effects on the female reproductive system or without the induction of birth defects on a living embryo. Thus, the effective use of angiogenesis inhibiting compounds for the inhibition of the female reproductive system was a surprising result.

AGM-1470 does not permanently impair the reproductive system as evidenced by the recovery of the reproductive system in the included examples. Chronic high dose administration of AGM-1470 blocks endometrial maturation and corpus luteal formation in sexually mature cycling mice. The examples of the present invention also show that angiogenesis inhibitors may disrupt follicular development in ovulation. Full recovery was seen 7 weeks after the drug was discontinued.

Single dose AGM-1470 treatment of mice one day after mating (but three days prior to implantation in the mouse) caused a failure of implantation induced angiogenesis and decidualization. This latter experiment demonstrates that the female reproductive tract can be disrupted by a single dose of angiogenesis inhibitors. Thus, low dose or single dose treatment is effective as a contraceptive (given before mating) without complete suppression of menstrual cycles or other systemic side effects. Furthermore, in the included experiments in which pregnant mice were treated with the angiogenesis inhibitor AGM-1470, birth defects were not documented when the drug was given during pregnancy.[27] High doses of AGM-1470 given in the first half of the pregnancy did block early placental formation resulting in a termination of the pregnancy. However, high doses given during the last half of pregnancy or low doses at various points throughout the pregnancy did not produce birth defects.

The present invention encompasses AGM-1470, fragments thereof, antisera thereof, receptor antagonists (including MetAP-2) or receptor agonists thereof that are combined with pharmaceutically acceptable exipients, and optionally sustained release compounds or compositions, such as biodegradable polymers, to form therapeutic compositions. These therapeutic compositions may be administered either to humans or animals, as applicable.

The present invention also relates to the application of angiogenesis inhibitors, such as AGM-1470, in a single dose or in multiple doses, to inhibit angiogenesis in the uterus, ovary, placenta, or fetus. In regulating angiogenesis related processes, an effective amount of the free form, or a salt of angiogenesis inhibitors, such as AGM-1470 can be used. Thus, angiogenesis inhibitors, such as AGM-1470, and salts thereof can be used for prophylaxis and/or treatment of neovascularization of endometriosis, adenomyosis, ovarian cysts, dysfunctional uterine bleeding, uterine leiomyoma (fibroids), choriocarcinoma and ectopic pregnancies.

As a result of the demonstration herein of the importance and controllable nature of angiogenesis in female reproductive tissues, the invention also provides methods of treating infertility disorders by promoting normal angiogenesis. Specifically, methods of treating infertility disorders are provided comprising administering to a female mammal an effective amount of an angiogenesis stimulator. Examples of angiogenesis stimulators include, vascular endothelial growth factors, fibroblast growth factors, tumor necrosis factors, transforming growth factors, thymidine phosphorylase, platelet derived growth factor, scatter factor, interleukin-8, granulocyte colony stimulating factor, angiogenin, platelet-activating factor, proliferin, substance P, lactate, hyaluron fragment, erucamide, and prostaglandins. The discussions of dosages, derivatives and pharmaceutical formulations of angiogenesis inhibitors herein is intended to apply also to angiogenesis stimulators.

It is to be understood that the present invention is contemplated to include any derivatives of the angiogenesis inhibitors that have endothelial inhibitory activity effective to regulate the female reproductive system. The present invention includes entire angiogenesis inhibiting compounds, derivatives of angiogenesis inhibiting compounds and biologically-active fragments of angiogenesis inhibiting compounds. These include proteins with angiogenesis inhibiting activity that have amino acid substitutions or have sugars or other molecules attached to amino acid functional groups. The present invention also includes genes that code for angiogenesis inhibiting proteins that are expressed by those genes. The angiogenesis inhibiting compounds described above can be provided as isolated and substantially purified in pharmaceutically acceptable formulations using formulation methods known to those of ordinary skill in the art.

These formulations can be administered by standard routes. In general, the combinations may be administered by the topical, transdermal, intraperitoneal, oral, rectal, vaginal, intrauterine, or parenteral (e.g., intravenous, subcutaneous or intramuscular) route. In addition, the angiogenesis inhibitor may be incorporated into biodegradable polymers allowing for sustained release of the compound, the polymers being implanted in the vicinity of where drug delivery is desired so that the angiogenesis inhibiting compound is slowly released systemically. The biodegradable polymers and their use are described, for example, in detail in Brem et al., *J. Neurosurg.* 74:441–446 (1991), which is hereby incorporated by reference in its entirety.

The dosage of the angiogenesis inhibiting compounds of the present invention will depend on the type of inhibitor being administered, disease state or condition being treated, and other clinical factors such as weight and condition of the human or animal and the route of administration of the compound. For treating female mammals with AGM-1470 for example, between approximately 0.05 mg/kg to 500 mg/kg, or preferably 0.1 to 100 mg/kg, of the angiogenesis inhibitor can be administered. For example in human females, approximately 1 mg/kg AGM-1470 can be administered, and in female mice approximately 30 mg/kg AGM-1470 can be administered. Depending on the use for which the drug is given and the preferences of the doctor administering and the patient receiving the compound, the angiogenesis inhibiting compound can be administered between several times per day to once a week. It is to be understood that the present invention has application for both human and veterinary use. The methods of the present invention contemplate single as well as multiple administrations, given either simultaneously or over an extended period of time.

The angiogenesis inhibiting compound formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Utilization of a Corneal Micropocket Model to Test AGM-1470 for the Ability to Inhibit Corneal Neovascularization Induced by bFGF or VEGF To confirm that angiogenesis was being inhibited, AGM-1470 was tested in vivo. A mouse corneal micropocket model was used which was recently developed to model tumor angiogenesis. Pellets of bFGF or VEGF were implanted in the mouse cornea resulting in aggressive neovascularization. AGM-1470 inhibited the amount of bFGF or VEGF induced neovascularization by 47% or 62% respectively (n=10/group p<0.001).

EXAMPLE 2

Treatment of Inseminated Mice with Single Dose AGM-1470

C57BL/6 male and female mice greater than seven weeks old were obtained from Takonic (Germantown, N.Y.). The mice were acclimated for at least five days prior to mating and housed in a twelve hour on and twelve hour off light schedule. The mice were mated in the evenings and vaginal plugs were checked for the next morning. Mating in mice is normally detected by the occurrence of vaginal plugs, which are formed by a mixture of the secretions of the vesicular and coagulating glands of the male and usually fill the vagina from cervix to vulva. The day of plugging was labeled Embryonic day 0 (E0). All animal studies were conducted according to the protocols approved by the Animal Ethics Committee of Children's Hospital. Plugged female mice were randomized and received either AGM- 1470 30 mg/kg s.c. or saline on E1, 7, or 14. The dependence of female reproductive system on angiogenesis was examined by treating sexually mature inseminated and cycling mice with selective angiogenesis inhibitor AGM-1470. The following results demonstrate that decidualization, placental formation, yolk sack development, and cyclical endometrial maturation are angiogenesis dependent.

Fetal Viability

One single dose of AGM-1470 resulted in 100% fetal resorption on E18 when injected either pre-implantation on E1 (n=69 embryos, p<0.0001) or post-implantation on E7 (n=36, p<0.0001). Since implantation in the mouse occurs on E4.5, these treatments correspond to inhibition of angiogenesis either before or after implantation. In contrast, normal litters were seen with AGM-1470 treatment on E14 (n=46) and control mice (n=104). Gross morphology of the uteri from mice treated on E1 or 7 and sacrificed before term, illustrated the failure of fetal growth and subsequent resorption. The pregnant mothers exhibited no signs of toxicity.

The dosing schedule of 30 mg/kg s.c. every other day was selected because this regiment produces no evident toxicity even after greater than 100 days of therapy and has demonstrated efficacy in suppressing tumors in mice. Mice were sacrificed on either E6, 9, 13 or 18 (one day prior to term gestation). Fetal viability was assessed and statistical analysis was performed with a Fisher's Exact Test.

Figure 2:
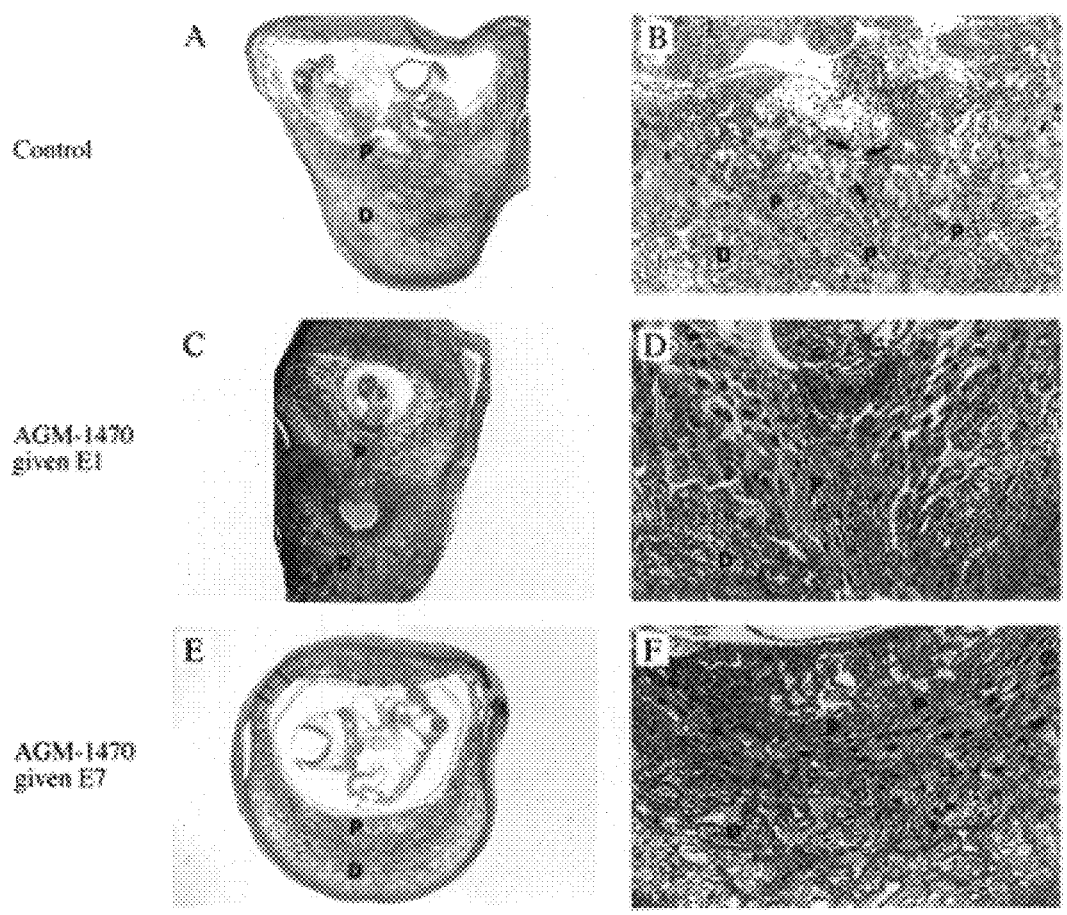
FIGS. 2A–2F show hematoxylin/eosin staining of mouse embryos on E9. Inseminated mice were treated with AGM-1470 mg/kg s.c. or saline on E1 or E7, and mice were sacrificed at E9. Uteri were resected and stained with hematoxylin/eosin as described in the material and methods section.

Mice given AGM-1470 on E7 showed an inhibition of placental and fetal development. Mice given AGM-1470 on E1 (four days prior to implantation) also had a failure of placental development. A possible explanation was that the endometrium exposed to AGM-1470 on E1 may be permanently altered so that although implantation occurs with trophoblast invasion, there is a failure of decidualization and coordinated development of the placenta. This hypothesis is supported by the observation of decreased endometrial microvessel density and decidual proliferation rate on E6, demonstrating a difference in endometrial response during trophoblast invasion. This inhibition of placental development inhibits further development of a viable fetus. See, FIG. 2.

When AGM-1470 was injected on E14 normal litters were delivered. This may be due to the fact that at the time point implantation, yolk sack formation, and placental development are already complete. Alternatively, since the placental barrier has been formed by E14, it may be capable of blocking transfer of AGM-1470 to the fetus.

Uterine Weight

Gravid uteri and ovaries were resected enbloc and weighed. Gravid uterine weight (grams wet weight, mean SE, n=3/day) in the control group increased exponentially from E6 ($0.20 \pm 0.01$), to E9 ($0.53 \pm 0.05$), E13 ($3.78 \pm 0.36$), and E18 ($12.87 \pm 0.62$). Gravid uterine weights from mice treated with AGM-1470 on E1 had no weight increase after E9 [E6 ($0.29 \pm 0.01$), E9 ($0.63 \pm 0.01$), E13 ($0.72 \pm 0.08$), $p<0.05$), and E18 ($0.68 \pm 0.02$, $p<0.05$)]. Gravid uterine weights from mice treated with AGM-1470 on E7 increased initially but then regresses after E13 [E9 ($0.71 \pm 0.01$), E13 ($2.03 \pm 0.14$, $p<0.05$), and E18 ($1.08 \pm 0.06$, $p<0.05$)].

Histology

Gravid uteri and ovaries were resected enbloc, weighed, fixed and Carnoy's fixative, and embedded in paraffin according to standard histological techniques. Sections were cut at 6 to 10 micrometers and stained with hematoxylin and eosin. When AGM-1470 was injected on E14, fetuses were allowed to come to term.

Fetal disorganization was seen in both AGM-1470 treated groups on E9 which was followed by necrosis on E13 and E18. In mice treated with AGM-1470 on E1 there was a failure of placental development. Although blood island formation appeared normal, there was an absence of the extension of these blood islands (angioblasts) into the fetal placenta. There were no nucleated red blood cells and no labyrinth structure in the placenta as compared to control. See FIG. 2F versus FIG. 2B. In mice treated with AGM-1470 on E7 there was a decrease in nucleated red blood cells and labyrinth structure in the placenta (FIG. 2D), and a marked decrease in nucleated red blood cells in the E9 embryos (See FIG. 2C). The ovaries appeared normal at all time points with the histologic evidence of mature corpora lutea.

When one single dose of AGM-1470 was given on E7, 2.5 days post-implantation, there was abnormal placenta and yolk development, as well as disrupted vascular development in the embryo. Loss of vascular development in the embryo could be due either to a direct effect of AGM-1470 on the embryonic vasculature or to a secondary effect caused by failure of normal placental and yolk sack development.

Although endothelial cell proliferation has been associated with corpora lutea maintenance during pregnancy, the fetal resorption produced when AGM-1470 was given at both E1 or E7 could not be accounted for by failure of the corpus luteal function. Histologic evidence of mature corpora lutea, along with normal serum progesterone levels provide evidence that ovarian function was maintained.

EXAMPLE 3

Implantation in Mice Treated With Single Dose AGM-1470 Pre-Implantation

The same procedures were followed as described above in Example 2 to administer 30 mg/kg AGM-1470 in single doses on the specified days. The mice were sacrificed and the number of implantation cites were counted. There was no decrease in the number of implantation cites when AGM-1470 was given on E1 [control mice had $8 \pm 0.2$ implants (n=29), mice injected with AGM-1470 on E1 had $9 \pm 0.4$ implants (n=16)]. Although there was no reduction in the number of embryos that implanted, the failure of placental development seen histologically at E9 could be secondary to abnormal changes in decidualization.

Figure 4:
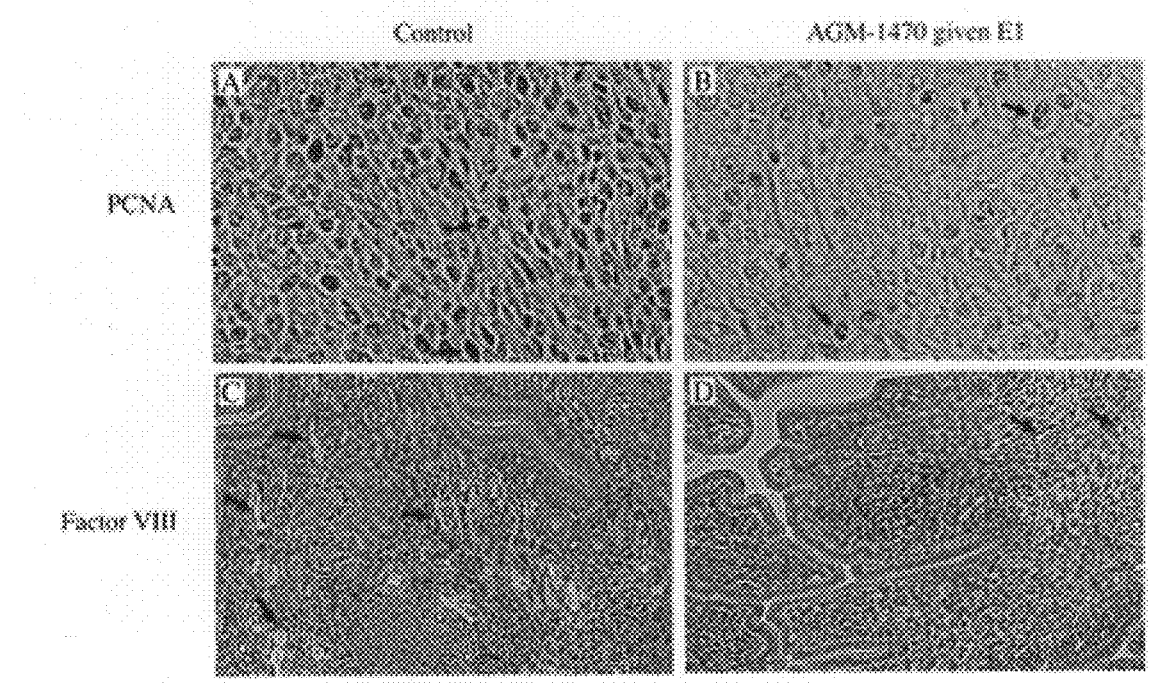
FIGS. 4A–4D shows the microvessel density of intersite endometrium and the proliferation rate of the decidua on E6. AGM-1470 30 mg/kg s.c. or saline was injected on E1 and uteri resected on E6 as described in the material and methods section.

To test this hypothesis, mice were treated with AGM-1470 on E1 and sacrificed at E6, a time point prior to placental formation. The uteri of the mice were examined by antibodies to Factor VIII and PCNA to determine if there was any difference in the degree of endometrial angiogenesis or the proliferative response of the decidua induced by trophoblast invasion. However, in the decidua there was a 50% decrease in the proliferation of stromal cells in the AGM-1470 treated mice as compared to control (PCNA staining/X630 field in control was $48\% \pm 3$, n=4, versus $24\% \pm 5$, n=4, $P \leq 0.005$ in AGM-1470 treated mice. See FIGS. 4A and 4B). There was also an associated 52% decrease in microvessel density in the intersite endometrium ($119 \pm 13$ vessels/X250 field in the control, n=4, versus $57 \pm 13$ vessels/X250 field in the AGM-1470 treated mice, n=4, $P \leq 0.05$. See FIGS. 4C and 4D).

These results demonstrate a reduction of endometrial angiogenesis and the proliferative response of the decidua induced by trophoblast invasion. Thus the inhibition of placental development in the mice given AGM-1470 on E1 may be attributable to alterations in the endometrium, so that although implantation occurs with trophoblast invasion, there is a failure of decidualization and coordinated development of the placenta.

EXAMPLE 4

Anti-CD31 Staining in Mice Treated With AGM-1470 Post-Implantation

Figure 5:
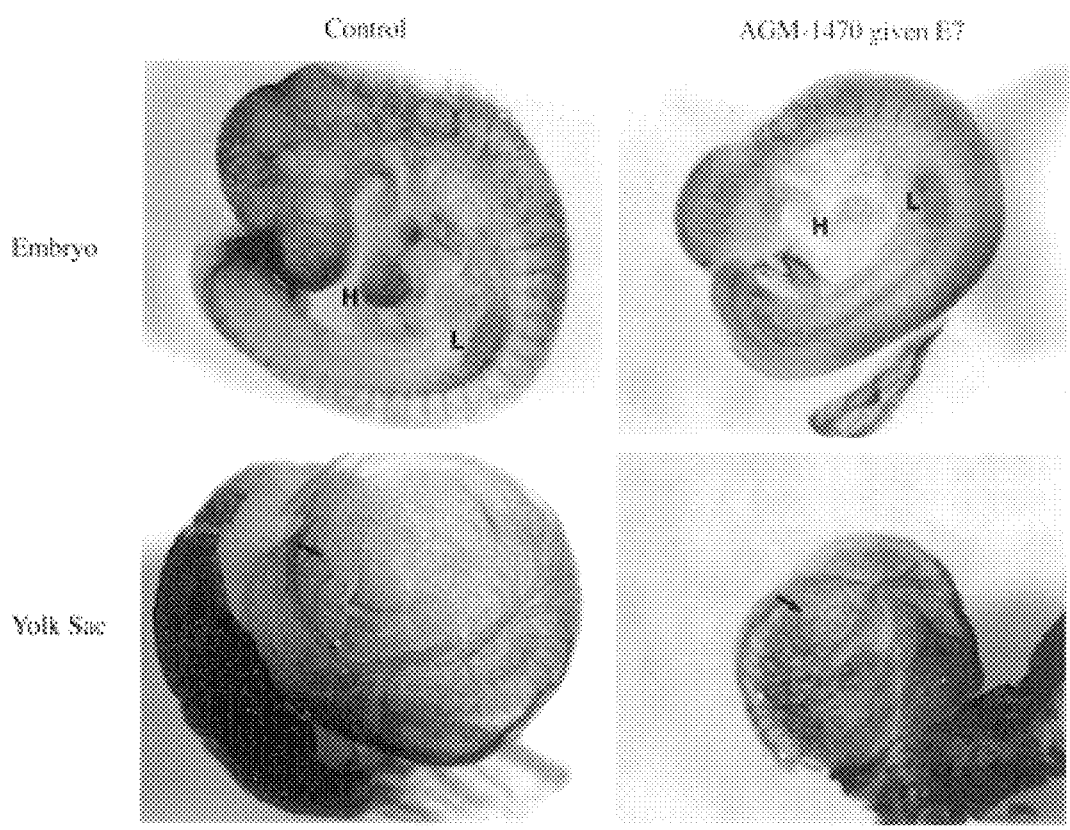
FIGS. 5A–5D show anti-DC31 vascular staining of the embryo and yolk sac on E9. The control and AGM-1470 (injected on E7) embryos were studied by whole mount immunohistochemistry for CD31/PECAM to stain blood vessels as described in the material and methods section. All panels were taken at the same magnification. The embryos treated with AGM-1470 on E7 were smaller and had a loss of capillary density (FIGS. 5A versus 5B). In some tissues such as the heart (H) and liver bud (L) there was almost a complete loss of CD31 labeled vessels. The yolk sac of AGM-1470 treated was also smaller and had a decrease in density and intercapillary distance of capillaries (arrows point to intercapillary spaces) (FIGS. 5C versus 5D).

Mice were treated with 30 mg/kg AGM-1470 following the same protocol in Example 2. The control and AGM-1470 treated embryos were studied on E9 by whole mount immunohistochemistry for CD-31/PECAM to stain blood vessels. The fetus and the yolk sack in the mice given AGM-1470 on E1 were excluded due to necrosis by E9. The embryos treated with AGM-1470 on E7 were smaller and had a diffuse decrease in capillary density. In the heart and liver bud, there was an almost complete loss of CD31 labeled vessels. See FIGS. 5A versus 5B. The yolk sack was also smaller and although vascular connections between blood islands were seen, there was decreased capillary density interconnecting the vessels. See FIGS. 5C versus SD. Loss of vascular development in the embryo could be due to either a direct effect of AGM-1470 on the embryonic vasculature or to a secondary effect caused by failure of normal placental and yolk sac development.

EXAMPLE 5

Serum Progesterone Levels Measured in Mice Treated with Single Dose AGM-1470 on Either E1 or E7

To determine whether any of the effects on the embryo and placenta were secondarily related to actions AGM-1470 might have had on the corpora lutea, the serum progesterone levels were measured on E9 in control and treated mice. This time point was chosen because histological evidence of involution was seen at E9 in both treated groups.

To determine whether corpora lutea function were intact in AGM-1470 treated pregnant mice, blood was collected at autopsy on E9 in control and mice treated with AGM-1470 30 mg/kg on E1 or E7. Blood was also collected from non-pregnant cycling mice in diestrus as a negative control. The blood was centrifuged for 10 minutes at 1000×g at 4° Celsius and the serum was stored at −20° Celsius until use. Serum progesterone was determined with a progesterone enzyme immunoassay test kit (Medics Biotech, Inc.) per manufacturer's instructions. The results were compared to a standard curve of human progesterone and data is measured a mean percent of control E9 progesterone level±s.e.m.

Serum from non-pregnant mice in diestrus served as a negative control. There was no decrease in serum progesterone levels in either treated group, with levels in mice treated with AGM-1470 on E1 or E7 measuring 112%±23 (n=3, NS), or 161%±24 (n=3, NS) of control, respectively. Serum from non-pregnant mice was 11%±2 (n=3, P≦0.001) of control. These data provide evidence that a loss of ovarian function was not induced after a single injection of AGM-1470 and thus not the cause of the loss of placental development.

EXAMPLE 6

Reversibility of AGM-1470 and Recovery of the Reproductive System

To establish long-term safety, the course of recovery of the reproductive system after fetal resorption was studied. Six plugged mice were injected with 30 mg/kg AGM-1470 on E1 (n=3) or E7 (n=3) and then anesthetized on E18 in a methoxyflurane (Pittman-Moore, Mandelein, Ill.) chamber so that a laparotomy could be performed. The uteri were inspected to confirm the presence of resorption cites. The incisions were closed with a running 3-0 ethelon™ black monofilament nylon suture (Ethicon, Somerville, N.J.). Animals were observed until fully recovered. After an additional six weeks the mice were remated to determine their ability to become inseminated and deliver a normal litter. The result was the production of normal litters in all mice. Additionally, the uteri of AGM-1470 treated mothers were grossly examined and appeared normal. Therefore, there is a functional recovery of the uterus after AGM-1470 treatment on E1 or E7.

The 30 mg/kg dose of AGM-1470 used produced no signs of toxicity to the mother in the experiments, and recovery of reproductive function was demonstrated by the birth of normal litters. Thus, decidualization and placental formation can effectively be disrupted with angiogenesis inhibitor without adverse effects to the mother's reproductive capacity.

EXAMPLE 7

Treatment of Inseminated Mice With Single Low Dose AGM-1470

The same protocol was followed as was performed for AGM-1470 30 mg/kg except mice were injected with only 3 mg/kg AGM-1470 on E1 or E7. The 10-fold lower dose was tested to determine if a dose in which the fetuses come to term would produce birth defects. Mice were sacrificed at E18 and fetal viability, number of implantation cites, crown-rump length, and tail length were assessed.

Since AGM-1470 caused an inhibition of placental development and fetal viability at a dose of 30 mg/kg, a 10-fold lower dose was tested to determine what effect a non-lethal dose would have on placenta and fetus. All fetuses at E18 were viable when AGM-1470 3 mg/kg was injected at E1 (n=21 fetuses) or E7 (n=8 fetuses). The fetuses were alive with no birth defects, but were smaller than normal. The crown-rump length on E18 relative to control (20.4±0.3 mm, n=13 embryos) was reduced by 36% in the AGM-1470 E1 (13.0±0.1 mm, n=7 embryos, p<0.0005), and 19% in the AGM-1470 E7 group (16.5±0.5 mm, n=7 embryos, p≦0.0005). Tail lengths were similarly effected with the reduction in lengths relative to control (11.4±0.2 mm, n=13 embryos) of 43% in the AGM-1470 E1 groups (6.5±0.2 mm, n=7 embryos, p≦0.0005) or 12% in the AGM-1470 E7 group (10.0±0.1 mm, n=7 embryos, p≦0.05).

EXAMPLE 8

Treatment of Cycling Mice With Chronic AGM-1470: Effect on Estrous Cycle

Female mice were housed individually in cages and acclimated for one week. The stage of the estrous cycles was checked by visual inspection of the vagina according to the criteria of Champlin[28] and the examiner was blinded to the treatment group. Determining the stage of the estrous cycle in the mouse by the appearance of the vagina.[1] Animals were monitored daily and graded for color, size of opening, striations and swelling. Based on these observations each individual was assigned to a cycle stage (diestrus, proestrus, estrus, or metestrus). Animals were monitored for 10 days prior to each experiment and animals not exhibiting a normal 4–5 day estrous cycle were excluded from the study.

Mice were randomized and received either AGM-1470 mg/kg s.c. or saline 0.1 ml s.c. every other day for 16 days (approximately four estrous cycles). On the last of four days of treatment mice were housed with male mice to see if successful mating and conception would occur. On day 16 mice were weighed and sacrificed by cervical dislocation. The ovaries were resected enbloc, fixed in Carnoy's fixative, and embedded in paraffin according to standard histologic techniques. Sections were cut at 6 microns and stained with hematoxylin and eosin.

During the experiment an additional morphology was observed in some of the mice. In these mice the vaginal opening was closed and the surrounding tissue was red, dry and non-edematous. The first occurrence of this morphology was after 5.6±3.2 days of treatment, and it was often interspersed with an abnormal, non-edematous diestrus-like appearance. After completion of the study the treatment code was unmasked. It was determined that the observation of this new morphology within 10 days of the start treatment correctly predicted AGM-1470 treatment in 8 of 8 mice whereas observation of at least one complete estrous cycle correctly predicted 8 out of 8 control mice. Thus, treatment with AGM-1470 caused an interruption of the normal estrous cycle with the presentation of different external morphology. None of the AGM-1470 mice were able to successfully mate as measured by no visually evident plugging as compared to a plugging rate in the control mice of 50% after 4 days. The changes in the external vagina morphology that may have prevented mating were only seen after treatment with AGM-1470 for several cycles (6 to 8 doses). Therefore, the use of a single dose could avoid these changes, exposing any potential contraceptive effects. However, given that one injection of AGM-1470 on E1 in inseminated mice produced similar changes in the endometrium (decreased angiogenesis and decidualization), which resulted in fetal resorption, it is likely that the suppression of angiogenesis and uterine gland and stromal proliferation seen in mice treated with AGM-1470 would persist after mating and also result in failure of decidualization.

Study of Immunohistochemistry

The whole-mount immunohistochemistry with monoclonal antibody to mouse PECAM (CD31) was performed essentially as described by Schlaeger[29] Embryos were dissected from the uterus and fixed in 4% paraformaldehyde, PBS at 4° Celsius overnight. The fixed embryos were subsequently rinsed in PBS at room temperature and dehydrated in a methanol series. The dehydrated embryos were bleached in 5% hydrogen peroxide in methanol for 4 to 5 hours at room temperature and then rinsed twice in methanol. Embryos were stored at −20° Celsius until used. The bleached embryos were rehydrated and blocked with PBSMT (3% instant skim milk, 0.1% Triton X-100, PBS) for one hour twice at room temperature. The embryos were then incubated with a 1:10 diluted hybridoma supernatant in PBSMT at 4° Celsius overnight. On the next day, the embryos were washed with PBSMT at 4° Celsius five times (1 hour each) and then incubated with a biotinylated secondary anti-rat IgG, mouse adsorbed (Vector Laboratories, Burlingame, Calif.) in PBSMT at 4° Celsius overnight. On the third day, the embryos were rinsed in PBSMT at 4° Celsius five times (1 hour each) and then incubated in avidin and horse radish conjugated biotin in PBSMT (1:100 dilution) (Vectastatin Elite Standard ABC Kit, Vector Laboratories) overnight at 4° Celsius. On the fourth day embryos were rinsed in PBSMT at 4° Celsius five time (1 hour each) and finally in PBT (0.2% BSA, 0.1% Triton-X100, PBS) for 20 minutes at room temperature. The peroxidase staining was performed by incubating embryos in 0.3 mg/ml DAB (Sigma), 0.5% $NiCl_2$ in PBT for 20 minutes followed by the $H_2O_2$ to the final concentration of 0.03% and incubated for 10 minutes. The staining reaction was stopped by rinsing in PBT and the PBS. The stained embryos were post-fixed in 2% paraformaldehyde, 0.1% glutaraldehyde in PBS at 4° Celsius overnight.

To determine microvessel density, Carnoy's-fixed tissue sections were pretreated with 2 microgram/ml Proteinase K (Boehringer Mannheim, Mannheim, Germany) at 37° Celsius for minutes before staining with a rabbit polyclonal antibody against mouse factor VIII (Dako, Carpinteria, Calif.). Positive staining was detected by incubating sequentially with a secondary antibody against rabbit conjugated to horseradish peroxidase (Dako) and diaminobenzidine tetrahydrochloride (DAB) (Dako) as a chromagen. Sections were counterstained with methyl green (Schmid & Co., Stuttgart, Germany) and mounted in Permount (Fisher, Fair Lawn, N.J.). Microvessel density was determined by light microscopy. Each count was expressed as the number of microvessels identified within a selected field. Ten fields per section were counted.

To determine the rate of cellular proliferation, staining for proliferating cell nuclear antigen (PCNA) was performed. Carnoy's-fixed sections were pretreated in target unmasking fluid (Signet Laboratories, Dedham, Mass.) for 10 minutes at 90° for antigen retrieval. Immunohistochemical staining was performed with an anti-PCNA murine monoclonal antibody (Signet). Positive staining was detected by using horse radish peroxidase-conjugated secondary (Dako) and tertiary (Dako) antibodies, and DAB as a chromagen. The PCNA labeling index was determined by counting the percentage of stained cells under light microscopy within selected 630× fields. A minimum of 1,000 cells were counted for each specimen.

For staining of apoptotic cells, Carnoy's-fixed sections were treated according to the protocol of the Apoptag manufacturer (Oncor, Gaithersburg, Md.) except the pretreatment step with Proteinase K was omitted. After TdT labeling of specimens, positive staining was detected with a peroxidase-labeled antibody against deoxyuridine peroxidase substrate. Sections were counterstained as described above. The apoptotic index was determined by counting the percentage of stained cells under light microscopy within selected 630× fields. A minimum of 1,000 cells was counted for each specimen.

In experiments with AGM-1470 treatment of pregnant mice, transverse sections through embryos contained within the uterus were stained. Microvessels density was determined at the intersite endometrium and PCNA was determined in the decidual stroma. In experiments with AGM-1470 treatment of non-pregnant mice, transverse sections through the endometrium were stained for factor VIII, PCNA or apoptotic cells at the level of the endometrial lumen at its widest diameter. Statistical analysis was performed with ANOVA on ranked data to account for the expected variation of endometrial angiogenesis and glandular proliferation in the control due to different phases of the estrous cycle.

Examination of the Uterus

Figure 6:
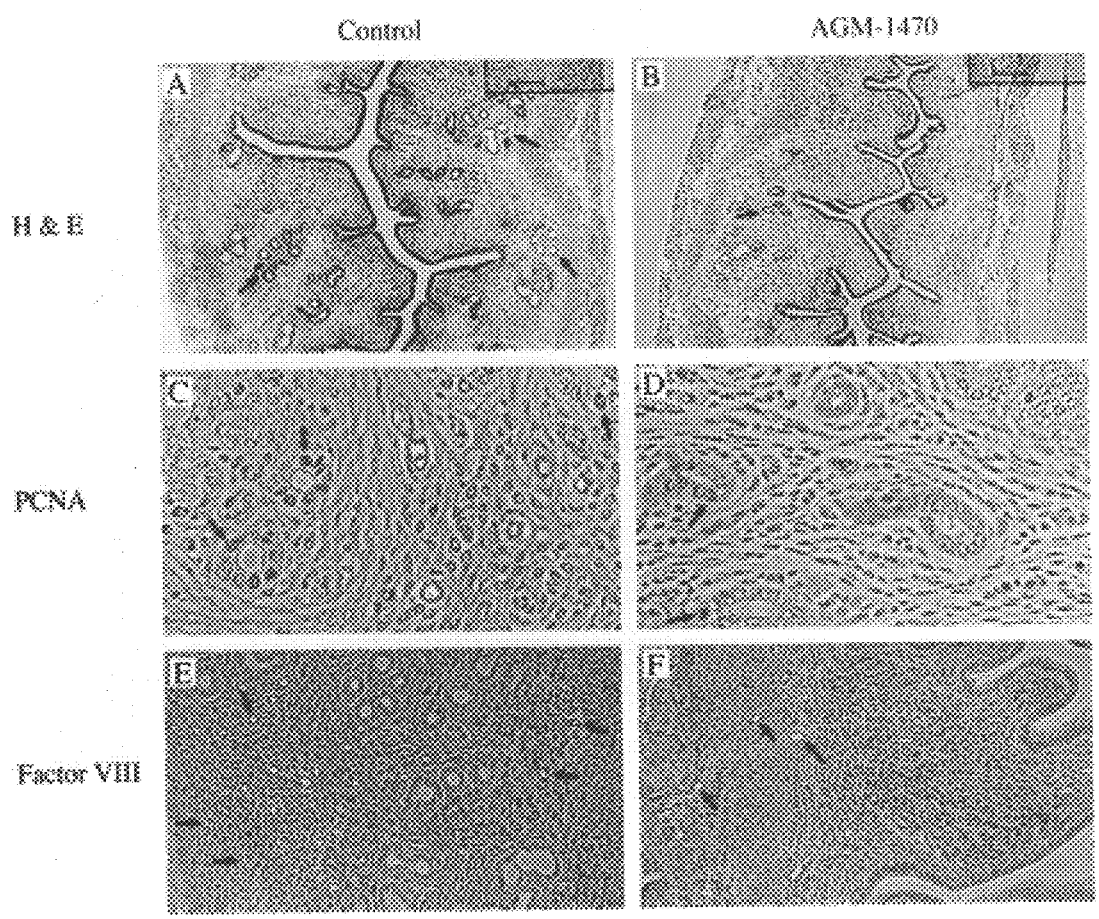
FIGS. 6A–6E shows the effect of AGM-1470 on the uterus of non-pregnant, cycling mice. Cycling mice were treated with AGM-1470 30 mg/kg s.c. every other day (n=8) for 16 days. a saline treated group (n=8) served as control. Uterus and ovaries were fixed in Carnoy's fixative and embedded in paraffin. Hematoxylin/eosin staining and immunohistochemistry to factor VIII and PCNA were performed as described in the material and methods section. The mice in the AGM-1470 treated group (FIG. 6B) had 63% fewer glands than the median of the control (FIG. 6A).

The uteri of treated mice were consistently thinner and contained fewer glands than the median of the untreated control mice. There was also a marked reduction in the proliferation of glandular epithelial and vascular endothelial cells. The ovaries were similarly impacted. The endometrium of the AGM-1470 30 mg/kg treated mice has 63% fewer glands than the control (median control had 35±3 glands/×250 field, n=8, AGM-1470 treated mice had 3±2 glands/×250 field, n=6, P≦0.005. See FIGS. 6A and 6B). To assess proliferation, sections of endometrium at comparable levels through the lumen of the uterus from treated and control mice were stained for PCNA. There was a 68% decrease in the proliferation rate of endometrial stromal cells (5%±2, n=6, P≦0.05) in AGM-1470 treated endometrium as compared to control mice (17%±3, n=5, FIGS. 6C and 6D). Similarly there was a 67% decrease in the percentage of proliferating glandular epithelial cells (10%±3, n=6, $P \leq 0.05$) in AGM-1470 treated endometrium as compared to control mice (30%±6, n=5). There was also a 71% decrease in the number of proliferating vessels/X630 field: (5±2, n=5, $P \leq 0.001$). Immunohistochemical staining using antibodies to Factor VIII (an endothelial cell specific marker), demonstrated a 41% decrease in the microvessel density in AGM-1470 treated mice versus control (17±2, n=6). See FIGS. 6E and 6F. The apoptotic index measured by Apo-Tag staining was low in both groups and not significantly different.

Examination of the Ovaries

Histologic examination of the ovaries in AGM-1470 mg/kg treated mice revealed the presence of Graafian follicles and corpora lutea. However, morphometric analysis revealed that the corpora lutea were fewer and 61% smaller in treated mice (mean cross sectional are of 0.038 $mm^2 \pm 0.006$, N=7, $P \leq 0.05$) when compared with control (0.097 $mm^2 \pm 0.014$, n=27) demonstrating that the luteal growth was limited.

Figure 3A:
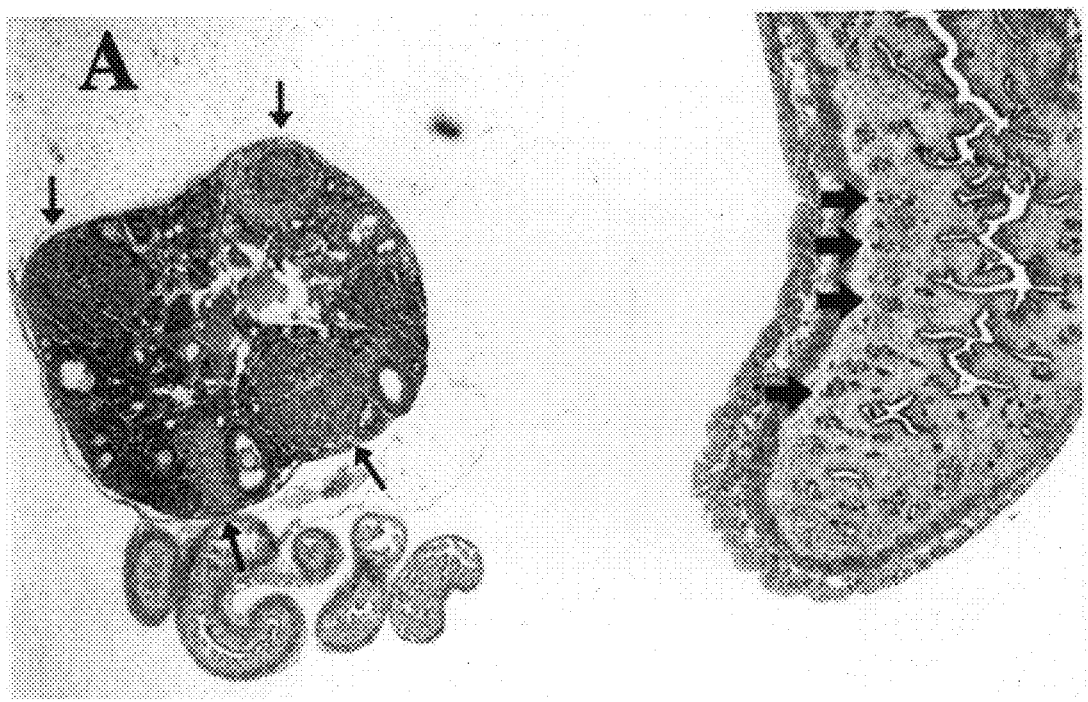
FIGS. 3A and 3B show ovaries and uteri from control and AGM-1470 chronically treated mice. Randomly cycling female C57BL/6 mice were chronically treated with AGM-1470 (30 mg/kg QOD, s.c.) for 16 days. Ovaries and uteri were removed en bloc, fixed and stained with hemotoxylin and eosin.
Figure 3B:
Figure 3C:
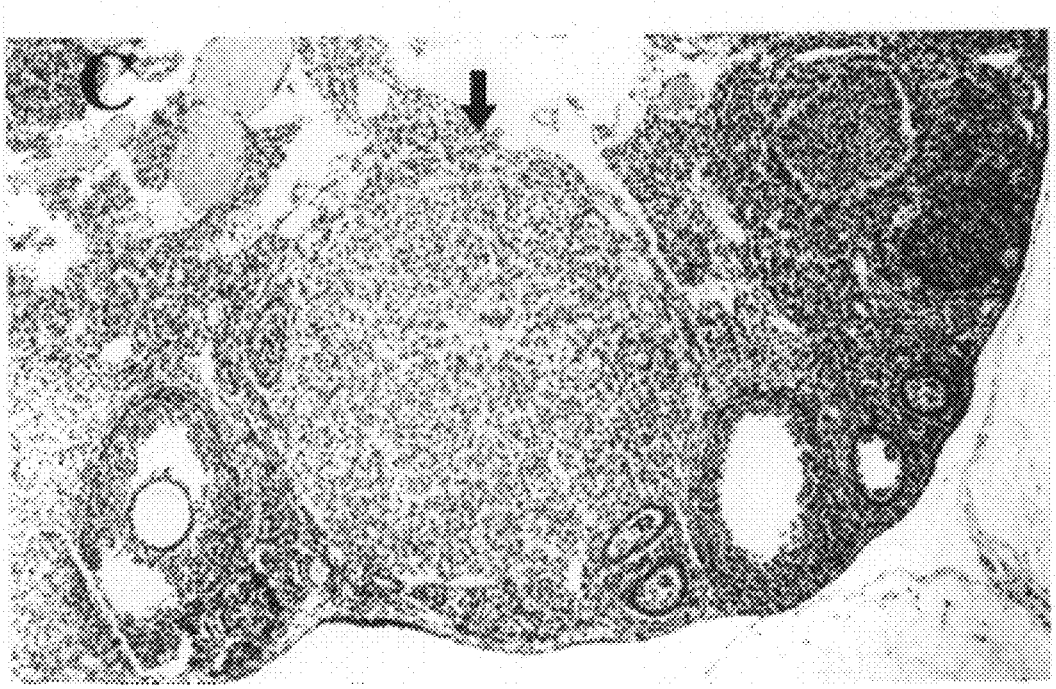
FIGS. 3C and 3D show ovaries and uteri from control and AGM-1470 chronically treated mice.
Figure 3D:
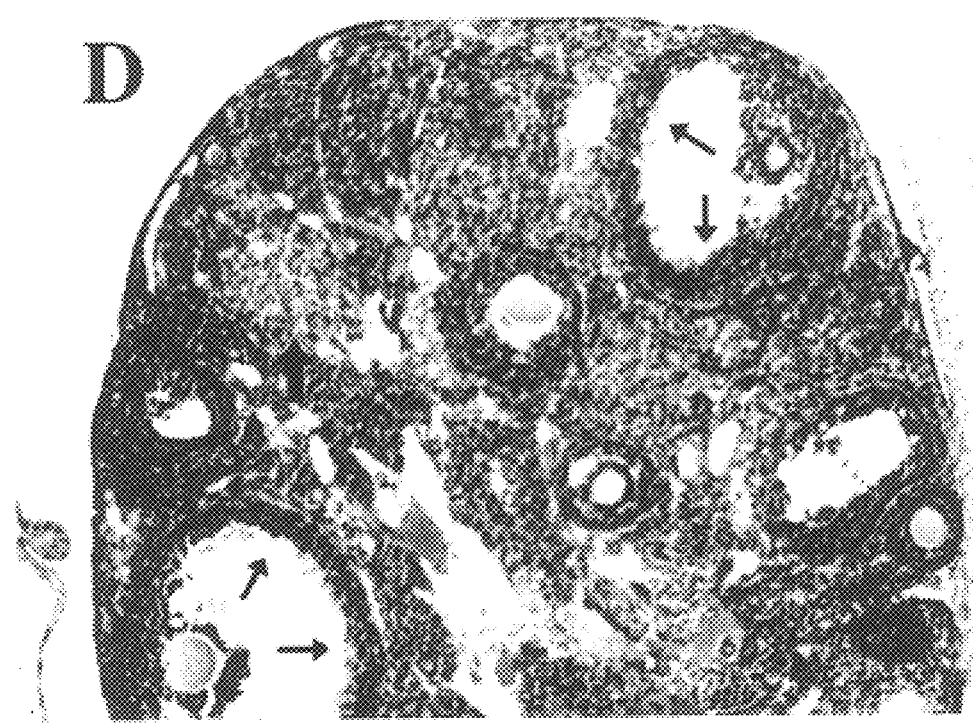

FIGS. 3A–3D show ovaries and uteri from control and AGM-1470 chronically treated mice. FIG. 3A shows tissue from control animal at 2.5× magnification. FIG. 3B shows tissue from AGM-1470 treated animal at 2.5× magnification. Note the decreased size and number of corpora lutea (small arrows) and number of endometrial glands (large arrows) in treated mice. FIG. 3C shows a close up of ovary section from FIG. 1A at 10× magnification showing corpora lutea (large arrows) and small antral follicles. FIG. 3D shows a close up of ovary from FIG. 1B at 10× magnification showing regressed corpora lutea and thin layer of granulosa cells in large antral follicles (small arrows).

Many corpora lutea in the treated mice were irregular in shape and almost completely regressed. These regressed corpora luteas made the remnants of ovulations occurring at the start of, or prior to, treatment. The ovaries of AGM-1470 treated mice also appeared to contain more antral follicles, but many of these follicles contained fewer than expected layers of granulosa cells suggesting that they are unhealthy.

EXAMPLE 9

Length of Time Between Application of AGM-1470 and Insemination Allowable for Maintained Effectiveness of AGM-1470

The experiment was designed to detect how long before mating a single dose of AGM-1470 might be effective. Sexually mature female mice were treated with a single dose of AGM-1470 (30 mg/kg, s.c.) up to five days prior to mating [designated E(−5), E(−4), E(−3), E(−2), E(−1), or E0 with the date of plugging being E0]. For treatments on E(−5) through E(−1), group-housed female mice were injected with AGM-1470 and then individually paired with male breeders at varying times after injection. For E0 treatment, females were paired with males and then plugged females were injected. Pregnancies were monitored by maternal weights and allowed to go to term. The contraceptive efficacy of a single dose of AGM-1470 on each of these days, calculated by the percentage of matings resulting in any viable deliveries decreased. The contraceptive efficacy of a single dose of AGM-1470 on each of these days, expressed as the percentage of matings resulting in viable deliveries is illustrated in FIG. 8

Effect of AGM-1470 on Number of Live Births

AGM-1470 had a dramatic effect on live births at certain time points. On E0 and E(−1), a single dose of AGM-1470 was able to completely block live births. Treatments on E(−2) reduced the percentage of animals with successful pregnancies by 80%. Three to five days prior to mating the effects of AGM-1470 appeared to have diminished with the treated mice having litters with the same frequency as controls. Decreased percentage of viable births in E(−4) is probably due to the small number of matings in that group. Experiments are ongoing to increase the number of animals in that group. Thus, a single dose of AGM-1470 appears to have its greatest effect when given within the first two days prior to mating. This corresponds to treatments on proestrus, estrus and metestrus. No differences in the number of dead births relative to controls was seen at any time point. See FIG. 8. It should be noted that female humans cycle on a 28 day interval, in contrast to the 4.5 day cycle of female mice, suggesting by extrapolation that human doses may be effective even several weeks prior to mating.

Figure 7A:
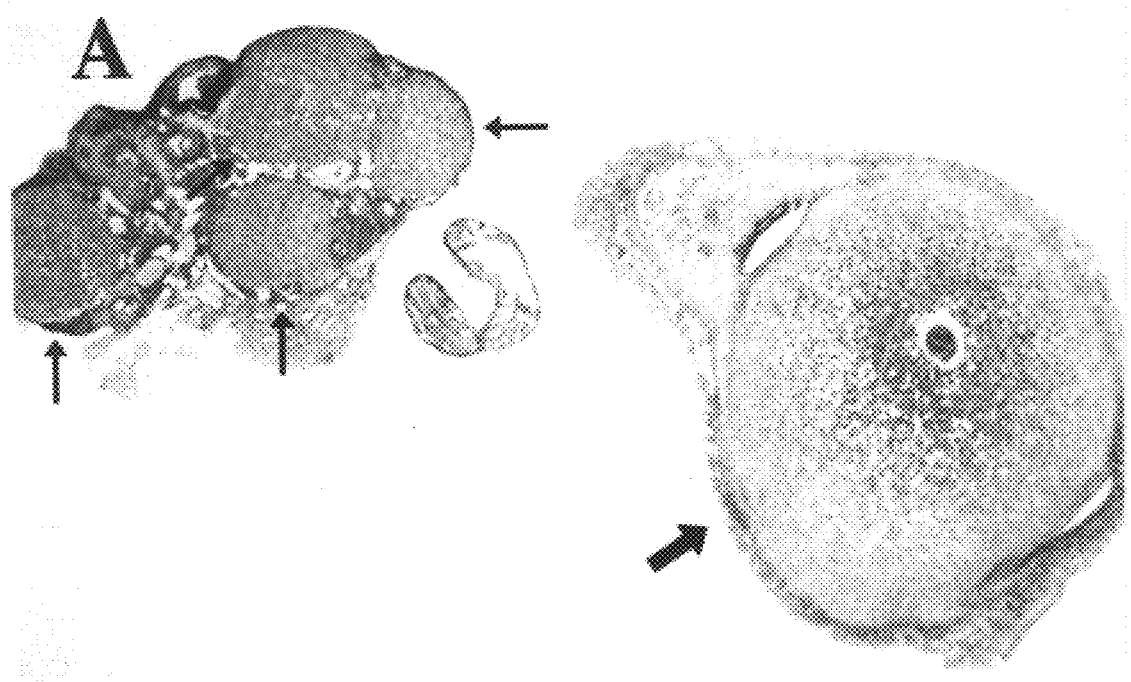
FIGS. 7A and 7B show the ovaries and uteri from a control mouse or an AGM-treated mouse given a single dose of AGM-1470 on E(−1). Group housed female C57BL/6 mice were treated with a single injection of AGM-1470 (30 mg/kg, s.c.) and paired with male breeders. Mice who mated on the day after treatment were sacrificed 6 days after mating. Ovaries and uteri were removed en bloc, fixed and stained with hemotoxylin and eosin.
Figure 7B:
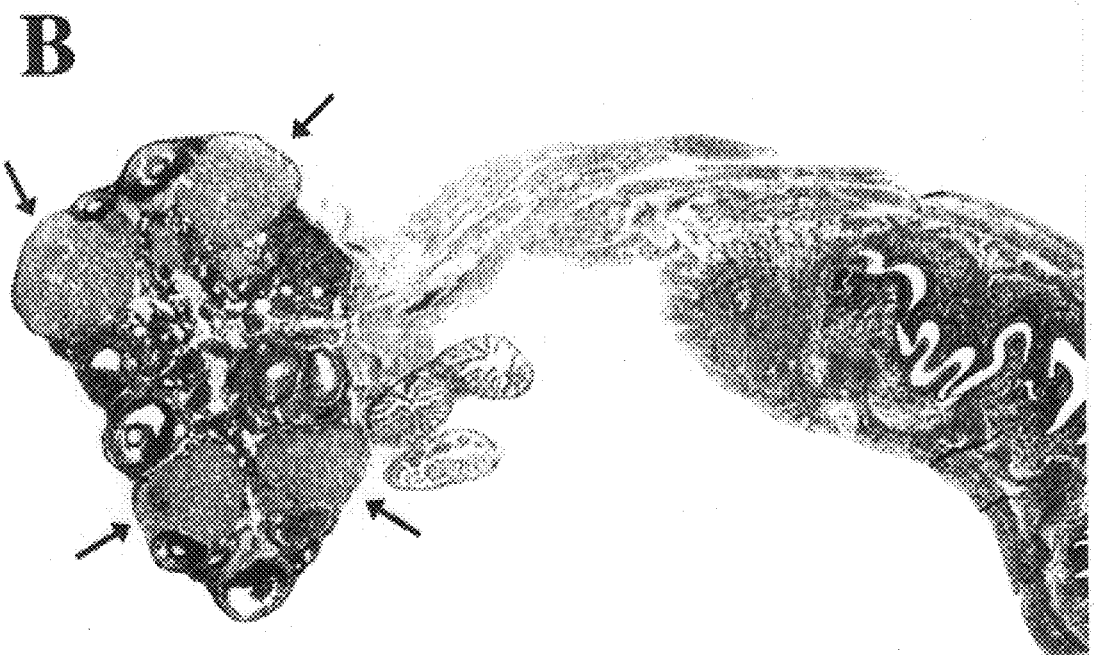

In addition, the ovaries and uteri from control and single treatment mice were examined. Group housed female C57BL/6 mice were treated with a single injection of AGM-1470 (30 mg/kg, s.c.) and paired with male breeders. Mice who mated on the day after treatment were sacrificed 6 days after mating. Ovaries and uteri were removed en bloc, fixed and stained with hemotoxylin and eosin. The results are demonstrated in FIG. 7. FIG. 7A shows tissue from control animal at 2.5× magnification. FIG. 7B shows tissue from AGM-1470 treated animal at 2.5× magnification. Thin arrows indicate the corpora lutea.I The fat arrows indicate implantation sites in control not seen in treated animal. Thus, the treatment with AGM-1470 prevented implantation.

These examples provide direct evidence that an angiogenesis inhibitor can regulate the female reproductive system, and in so doing provides a novel method for controlling fertility. Decidualization, placental formation, yolk sac development, cyclical endometrial maturation, ovulation and corpora lutea growth are angiogenesis dependent and the invention provides a novel method for controlling fertility. Additionally, the inhibitory effects of AGM-1470 on endometrial angiogenesis, stromal and glandular proliferation, as well as placental formation, provides methods for treating several pathologic reproductive processes such as endometriosis, adenomyosis, dysfunctional uterine bleeding, choriocarcinoma, uterine leiomyoma (fibroids), and ectopic pregnancy.

All of the references mentioned herein are hereby incorporated by reference in their entireties.

References

1. Poole, T. J. & Coffin, J. D., Vasculogenesis and angiogenesis- two distinct morphogenetic mechanisms establish embryonic vascular pattern. *J. Exp. Zool.* 251: 224–31 (1989).
2. Gospodarowicz, D. & Thanral, K. K., Production of a corpus luteum angiogenic factor responsible for the proliferation of capillaries and neovascularization of the corpus luteum. *Proc. Natl. Acad. Sci. USA* 75: 847–51 (1978).
3. Ravindranath, N., Little-Ihrig, L., Phillips, H. S., Ferrara, N., & Zeleznick, A. J., Vascular endothelial growth factor mRNA expression in the primate ovary. *Endocrinol.* 131: 254–260 (1992).
4. Christenson, L. K. & Stouffer, R. L., Proliferation of microvascular endothelial cells in the primate corpus luteum during the menstrual cycle and simulated early pregnancy. *Endocrinol.*, 137: 367–74 (1996).
5. Tamura, H. & Greenwals, G. S., Angiogenesis and its hormonal control in the corpus luteum of the pregnant rat. *Biol. Reprod.* 36: 1149–1154 (1987).
6. Torry, R. J. & Rongish, B. R., Angiogenesis in the uterus: potential regulation and relation to tumor angiogenesis. *Am. J. Reprod. Immunol.* 27: 171–179 (1992).

7. Christofferson, R. & Nilsson, B. O., Morphology of the endometrial microvasculature during early placentation in the rat. *Cell Tissue Res.* 253: 217–224 (1988).
8. Greenwald, G. S., Temporal and topographical changes in DNA synthesis after follicular atresia. *Biol. Reprod.* 40: 175–181 (1989).
9. Redmer, D. A., Rone, J. D., & Goodman, A. L., Evidence for a non-steroidal angiotropic factor from the primate corpus luteum: Stimulation of endothelial cell migration in vitro. *Proc. Soc. Exp. Biol. Med.* 179:136–140. (1985).
10. Koos, R. D. & LeMaire, W. J., Factors that may regulate the growth and regression of blood vessels in the ovary. *Semin. Reprod. Endocrinol* 1:295–307 (1983).
11. Jakob, W., Jentzch, B., Mauersberger, B., & Oehme, P., Demonstration of angiogenesis activity in the corpus luteum of cattle. *Exper. Pathol.* 13:231–36 (1977).
12. Ravindranath, N., et al.(1996), supra. Tsukada, K., Matsushima, T., Yamanaka, N., Neovascularization of the corpus luteum during the estrus cycle. *Path. Internat.* 46(6): 408–416 (1996).
13. *Biol. Reprod.* 36: 1149–1154 (1987).
14. Zeleznik, A. J., Schuler, L. E., & Reichert, J. R., Gonadotropin-binding sites in the rhesus monkey ovary: role of the vasculature in the selective distribution of human chorionic gonadotropin to the preovulatory follicle. *Endocrinol.* 109:356–62 (1981).
15. Koos, R. D. & Olson, C. E., Expression of bFGF in the rat ovary: Detection of mRNA using reverse transcription-polymerase chain reaction amplification. *Mol. Endocrinol.* 3:2041–8 (1989).
16. Neufeld, G., Ferrara, N., Schweigerer, L., Mitchel, R., & Gospodarowicz, D., Bovine granulosa cells produce bFGF. *Endocrinol.* 121:597–603 (1987).
17. Yanagashita, M., Hascall, V., & Rodbard, D., Biosynthesis of proteoglycans by rat granulosa cells cultured in vitro: Modulation by gonadotropins, steroid hormones, prostaglandins and cyclic nucleotide. *Endocrinol.* 109:1641–9 (1981).
18. Ferrara, N. & Henzel, W. J., Pituitary follicular cells secrete a novel heparin-binding growth factor specific for vascular endothelial cells. *Biochem. Biophys. Res. Comm.* 161: 851–858 (1989).
19. Gospodarowicz, D. Abraham, J .A. & Schilling, J. Isolation and characterization of a vascular endothelial mitogen produced by pituitary-derived folliculo stellate cells. *Proc. Natl. Acad. Sci. USA* 86: 7311–7315 (1989).
20. Connolly, D. T., et al. Human vascular permeability factor. Isolation from U937 cells. *J. Biol. Chem.* 264: 20017–20024 (1989).
21. Keck, P. J. et al. Vascular permeability factor, an endothelial cell mitogen related to PDGF. *Science* 246: 1309–1312 (1989).
22. Kamat, B. R., Brown, L., Manseau, E., Senger, D. & Dvorak, H., Expression of VPF/VEGF by human granulosa and theca lutein cells *Am. J. Pathol.* 146:157–165 (1995).
23. Shweiki, D., Itin, A., Neufeld, G., Gitay-Goren, H., & Keshet, E . Patterns of expression of vascular endothelial growth factor and VEGF receptors in mice suggest a role in hormonally regulated angiogenesis. *J. Clin. Invest.* 91:2235–2243 (1995).
24. Goodger, A. M. & Rogers, P. A., Uterine endothelial proliferation before and after embryo implantation. *J. Reprod. Fertility* 99: 451–7 (1993).
25. Folkman, J. & Klagsbrun, M. Angiogenic factors. *Science* 235: 442–447 (1987).
26. Ingber, D. et al. Synthetic analogues of fumagillin that inhibit angiogenesis and suppress tumor growth. *Nature* 348, 555–557 (1990).
27. Abe, J. et al. A fumagillin derivative anaioaenesis inhibitor, AGM-1470, inhibits activation of cyclin-dependent kinases and phosphorylation or protooncogene expression in vascular endothelial cells. *Cancer Res.* 54: 3407–3412 (1994).
28. D'Amato, R .J., Loughnan, M. S., Flynn, E., & Folkman, J., (1994) Thalidomide is an inhibitor of angiogenesis. *Proc. Natl. Acad. Sci. USA* 91: 4082–4085.
27. Klauber, N., Rohan, R., Flynn, E., D'Amato, R. J., Critical components of the female reproductive pathway are suppressed by the angiogenesis inhibitor AGM-1470. *Nature *-Med.* 3(4): 443–446, (1997).
28. Champlin, A. K., Dorr, D. I., & Gates, A. H., *Biol. Reprod.* 8:491–494 (1973).
29. Schlaeger, T. M., Qin, Y., Fujiwara, Y., Magram, J. & Sato, T. N., Vascular endothelial cell lineage-specific promoter in transgenic mice. *Development* 121: 1089–1098 (1995).

We claim:

1. A method of regulating fertility in a female mammal, in need of such regulation, comprising administering to such female an angiogenesis inhibiting, and fertility regulating amount of AGM-1470.

2. The method of claim 1, wherein the angiogenesis inhibiting compound is administered to prevent conception.

3. The method of claim 1, wherein the angiogenesis inhibiting compound is administered to terminate a pregnancy.

4. The method of claim 1, wherein angiogenesis is inhibited in the uterus, ovary, placenta or fetus.

5. The method of claim 1, wherein the angiogenesis inhibiting compound is an antagonist of the AGM-1470 receptor MetAP-2.

6. The method of claim 1, wherein the angiogenesis inhibiting compound is administered in a single dose or in multiple doses.

7. The method of claim 1, wherein angiogenesis is inhibited prior to, during, or after decidualization, placental formation, yolk sac or fetal development.

8. The method of claim 1, wherein the angiogenesis inhibiting compound is administered prior to intercourse, after intercourse or after ovum fertilization.

* * * * *